United States Patent
Nagashima et al.

(10) Patent No.: US 10,012,583 B2
(45) Date of Patent: Jul. 3, 2018

(54) REFLECTION PROPERTIES MEASURING DEVICE AND MANUFACTURING METHOD FOR POLARIZING PLATES USED IN SAME

(71) Applicant: KONICA MINOLTA, INC., Tokyo (JP)

(72) Inventors: Yoshiyuki Nagashima, Sakai (JP); Katsutoshi Tsurutani, Osaka (JP)

(73) Assignee: Konica Minolta, Inc., Tokyo (JP)

( * ) Notice: Subject to any disclaimer, the term of this patent is extended or adjusted under 35 U.S.C. 154(b) by 392 days.

(21) Appl. No.: 14/648,577

(22) PCT Filed: Sep. 11, 2013

(86) PCT No.: PCT/JP2013/006781
§ 371 (c)(1),
(2) Date: May 29, 2015

(87) PCT Pub. No.: WO2014/083798
PCT Pub. Date: Jun. 5, 2014

(65) Prior Publication Data
US 2015/0323446 A1    Nov. 12, 2015

(30) Foreign Application Priority Data

Nov. 30, 2012    (JP) ................... 2012-262285

(51) Int. Cl.
*G01N 21/21* (2006.01)
*G01N 21/25* (2006.01)
*G01N 33/32* (2006.01)

(52) U.S. Cl.
CPC ........... *G01N 21/21* (2013.01); *G01N 21/251* (2013.01); *G01N 33/32* (2013.01); *G01N 2201/063* (2013.01)

(58) Field of Classification Search
CPC ...... G01N 21/21; G01N 21/251; G01N 21/55; G01N 21/5907; G01N 21/5911;
(Continued)

(56) References Cited

U.S. PATENT DOCUMENTS 7,006,223 B2 * 2/2006 Mullani ............... A61B 5/0059
356/369
7,027,153 B2 * 4/2006 Mullani ............... A61B 5/0059
356/369
(Continued)

FOREIGN PATENT DOCUMENTS

| JP | 57-192841 | 11/1982 |
| JP | 61-101722 | 6/1986 |

(Continued)

OTHER PUBLICATIONS

Office Action dated Feb. 2, 2016 which issued in the corresponding Japanese Patent Application No. 2014-549795.

*Primary Examiner* — Kara E Geisel
*Assistant Examiner* — Violeta A Prieto
(74) *Attorney, Agent, or Firm* — Cozen O'Connor

(57) ABSTRACT

A reflection property measuring device comprising illumination light and reflected light polarizing plates held by a holder in a mutually superposed state in a thickness direction thereof, wherein the holder has a fittingly-holding portion for setting a held posture, and each of the polarizing plates has a fitting portion fittable to the fittingly-holding portion. The fitting portions of the polarizing plates are provided at positions allowing the polarizing plates to be held by the holder in respective postures where polarizing directions thereof intersect orthogonally. A manufacturing method is disclosed for polarizing plates used in the device, wherein the illumination light and reflected light polarizing plates are
(Continued)

manufactured in such a manner as to be punched out from the same polarizing plate material.

8 Claims, 11 Drawing Sheets

(58) Field of Classification Search
CPC .............. G01N 2021/5915–2021/5996; G01J 2003/516; G01J 3/513
See application file for complete search history.

(56) References Cited

U.S. PATENT DOCUMENTS

| | | | | |
|---|---|---|---|---|
| 7,167,243 B2* | 1/2007 | Mullani | ............... | A61B 5/0059 356/369 |
| 7,167,244 B2* | 1/2007 | Mullani | ............... | A61B 5/0059 356/369 |
| 9,458,990 B2* | 10/2016 | Mullani | ..................... | F21V 9/14 |
| 2004/0174525 A1* | 9/2004 | Mullani | ............... | A61B 5/0059 356/369 |
| 2004/0201846 A1* | 10/2004 | Mullani | ............... | A61B 5/0059 356/369 |
| 2006/0132774 A1* | 6/2006 | Mullani | ............... | A61B 5/0059 356/369 |
| 2006/0139640 A1* | 6/2006 | Mullani | ............... | A61B 5/0059 356/369 |
| 2014/0243685 A1* | 8/2014 | Patwardhan | ............. | A61B 5/44 600/476 |
| 2015/0036311 A1* | 2/2015 | Mullani | ..................... | F21V 9/14 362/19 |

FOREIGN PATENT DOCUMENTS

| | | |
|---|---|---|
| JP | 2010-139824 | 6/2010 |
| WO | WO2011/093024 | 8/2011 |
| WO | WO2012/101922 | 8/2012 |

* cited by examiner

REFLECTION PROPERTIES MEASURING DEVICE AND MANUFACTURING METHOD FOR POLARIZING PLATES USED IN SAME

RELATED APPLICATIONS

This is a U.S. National Phase Application under 35 USC 371 of International Application No. PCT/JP2013/006781 filed on Nov. 19, 2013.

TECHNICAL FIELD

The present invention relates to a reflection property measuring device for measuring a reflection property of a sample surface, for example, for color evaluation of a printed matter, and a method of manufacturing polarizing plates for use in the reflection property measuring device.

BACKGROUND ART

Control of print quality in a printed matter (e.g., ink color adjustment) is performed by measuring a reflection property such as a print density or color values of ink on a CMYK (Cyan, Magenta, Yellow, Black) test patch. For example, a print density of ink is measured according to ISO 5-4. In this measurement, a so-called 45/0 geometry in which illumination light is emitted in a direction at 45° with respect to a normal line to a sample surface (in a 45-degree direction), and, among reflected light rays reflected by the sample surface, a reflected light ray in the normal line is received, or a so-called 0/45 geometry in which the illuminating direction and the light-receiving direction are interchanged with each other.

In order to quickly respond to a change in ink concentration during printing to thereby suppress the occurrence of a defective product, it is necessary to measure a print density of ink just after printing. However, when ink in an undried state just after printing is dried, the print density changes due to dry-down. Thus, the print density of the ink just after printing cannot be directly compared to a density of a reference sample which is in a dried state. The term "dry-down" here means a phenomenon that, along with drying of ink on a printing matter, a print density of the ink after being dried drops down, as compared to a print density of the ink just after printing. This dry-down is caused by a difference between reflection of light on a surface of an ink layer just after printing (a layer of ink formed on a sheet surface by printing), and reflection of the light on a surface of the ink layer in a dried state of the ink. More specifically, in the state just after printing, the ink layer has a flat and smooth surface, irrespective of irregularities of the sheet surface, so that illumination light emitted in a 45-degree direction is specularly or regularly reflected by the flat and smooth surface of the ink layer, and the reflected illumination light does not enter a light-receiving system capable of receiving a reflected light ray in a 0-degree direction (direction of a normal line to the sheet surface). On the other hand, in the state after the ink is dried, the ink layer has a surface conforming to irregularities of the sheet surface (i.e., a surface with a concavo-convex shape), so that the illumination light is scatteredly or irregularly reflected by the concavo-convex surface of the ink layer, and a part of the reflected illumination light enters the light-receiving system. This causes the dry-down.

Therefore, in a conventional density measurement, two polarizing plates whose polarizing directions (polarizing axes, polarization properties) mutually intersect orthogonally are inserted, respectively, into an illuminating optical system and a light-receiving optical system, and, in this state, the print density is measured. This eliminates an influence of the dry-down to thereby allow a print density of ink just after printing to be effectively compared with the density of the reference sample. In this density measurement, by utilizing a phenomenon that a polarization characteristic of illumination light after being polarized by the polarizing plate inserted in the illumination optical system is maintained even in the illumination light after being reflected by the surface of the ink layer in the dried state, the polarizing plate inserted in the light-receiving optical system blocks (prevents) the illumination light after being regularly reflected by the surface of the ink layer from entering the light-receiving optical system.

For example, in the following Patent Literature 1, as illustrated in FIG. 11, a measurement is performed using a polarizing plate 100 formed by bonding a circular ring-shaped first polarizing plate 101 and a circular-shaped second polarizing plate 102 disposed in a central region of the first polarizing plate 101 together in such a manner as to allow polarizing directions thereof to mutually intersect orthogonally. In the measurement, a reflection property of a sample surface s is measured under a condition that illumination light 103 is passed through the second polarizing plate 102, and the illumination light after being reflected by the sample surface s (reflected light 104) is passed through the first polarizing plate 101. In this manner, the first polarizing plate 101 and the second polarizing plate 102 whose polarizing directions mutually intersect orthogonally are arranged in adjacent relation, so that it becomes possible to arrange an illumination optical system and a light-receiving optical system in adjacent relation to achieve a reduction in size of a reflection property measuring device.

In the measurement of the reflection property of the sample surface s, in order to ensure sufficient measurement accuracy, it is necessary to allow the polarizing direction (polarizing axis) of the second polarizing plate 102 for passing the illumination light 103 therethrough to accurately intersect orthogonally with the polarizing direction (polarizing axis) of the first polarizing plate for passing therethrough the reflected light 104 as the illumination light after being reflected by the sample surface s 103. For example, the ISO Standard specifies that the accuracy should fall within ±5°.

However, the polarizing plates 101, 102 are arranged such that the small circular-shaped second polarizing plate 102 is disposed radially inside the first polarizing plate 101. Thus, during bonding between the first polarizing plate 101 and the second polarizing plate 102, it was difficult work to allow the respective polarizing directions thereof to accurately intersect orthogonally.

CITATION LIST

Patent Literature

Patent Literature 1: JP 57-192841A

SUMMARY OF INVENTION

The present invention has been made in view of the above circumstances, and an object thereof is to provide a reflection property measuring device capable of, when a polarizing plate for passing illumination light therethrough and a polarizing plate for passing reflected light therethrough are arranged with respect to each other, allowing respective polarizing directions thereof to intersect orthogonally in an accurate and easy manner, and a method of manufacturing polarizing plates for use in the reflection property measuring device.

In a reflection property measuring device of the present invention, an illumination light polarizing plate inserted in an illuminating optical system for guiding illumination light to a sample surface, and a reflected light polarizing plate inserted in a light-receiving optical system for guiding reflected light as the illumination light after being reflected by the sample surface, to a light detection section, are held by a holder in a mutually superposed state in a thickness direction thereof. The holder has a fittingly-holding portion for setting a held posture, and each of the illumination light polarizing plate and the reflected light polarizing plate has a fitting portion fittable to the fittingly-holding portion of the holder. The fitting portions are provided at positions allowing the illumination light polarizing plate and the reflected light polarizing plate to be held by the holder in respective postures where polarizing directions thereof intersect orthogonally. In a method of manufacturing polarizing plates used in the reflection property measuring device, of the present invention, the illumination light polarizing plate and the reflected light polarizing plate are manufactured by punching out the illumination light polarizing plate and the reflected light polarizing plate from the same polarizing plate material using a first die for the illumination light polarizing plate and a second die for the reflected light polarizing plate. Therefore, the reflection property measuring device and the polarizing plate manufacturing method are capable of, when the illuminating polarizing plate and the reflecting polarizing plate are installed, establishing orthogonality between respective polarizing directions thereof in an accurate and easy manner.

The above and other objects, features and advantages of the present invention will be apparent from the following detailed description and the accompanying drawings.

DESCRIPTION OF EMBODIMENTS

Figure 1:
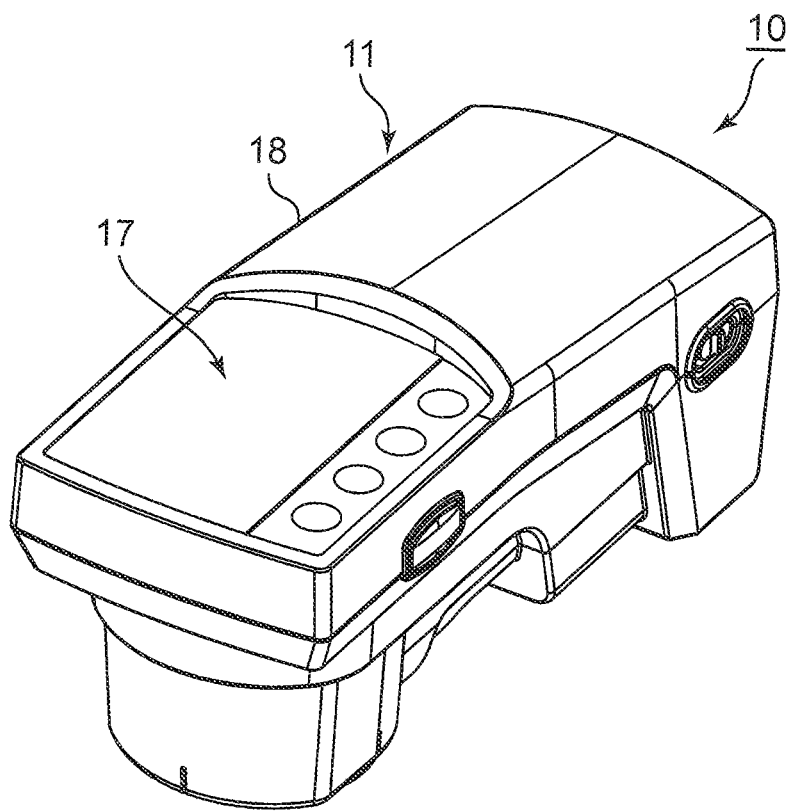
FIG. 1 is a perspective view of a color densitometer according to one embodiment of the present invention, when viewed from an upper side thereof.

Based on the drawings, one embodiment of the present invention will now be described. In the figures, elements or components assigned with the same reference numeral or sign mean that they are the same, and duplicated description thereof will be appropriately omitted. In this specification, a collective term will be denoted by a reference numeral or sign from which a suffix is omitted, and a term indicative of an individual element or component will be denoted by a reference numeral or sign with a suffix.

Figure 2:
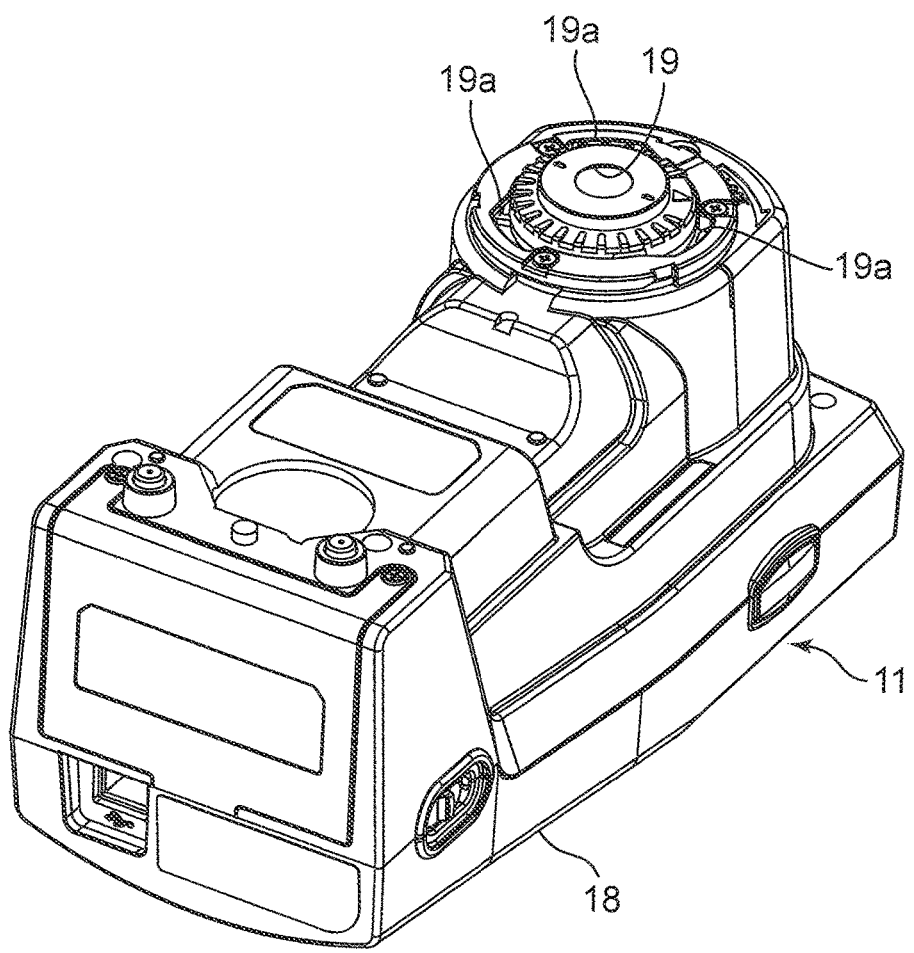
FIG. 2 is a perspective view of the color densitometer, when viewed from a lower side thereof, wherein a polarization filter unit is detached therefrom.
Figure 3:
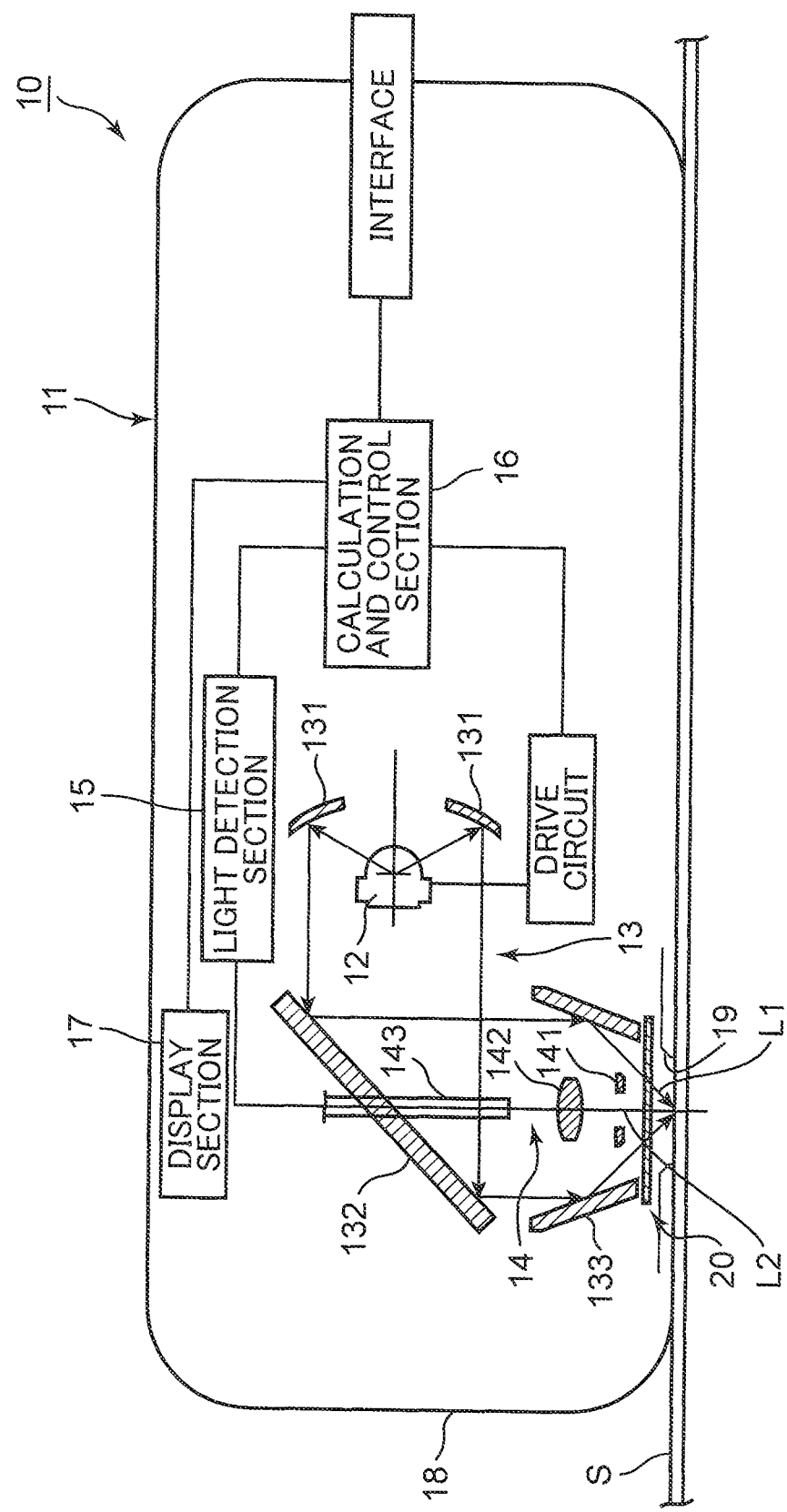
FIG. 3 is a block diagram illustrating a structure of the color densitometer.
Figure 4:
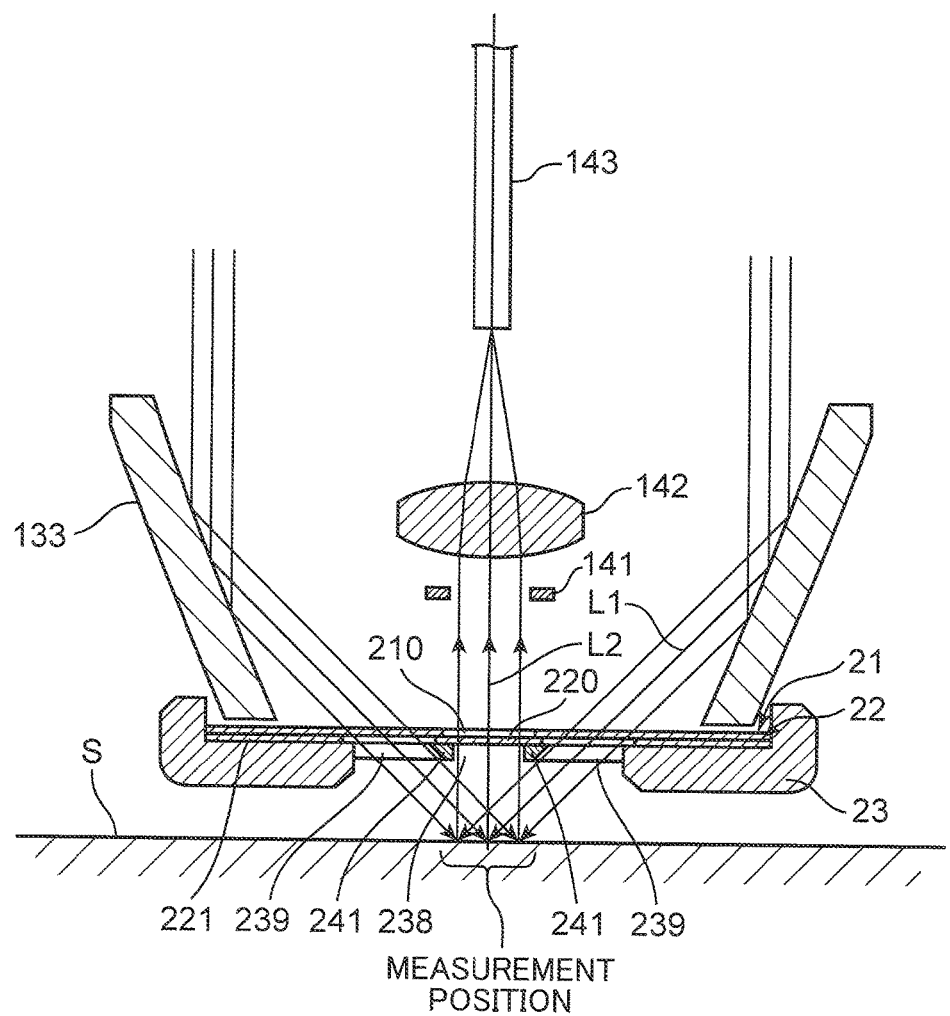
FIG. 4 is an enlarged explanatory diagram of optical paths of illumination light and receiving light in the vicinity of a polarization filter unit in FIG. 3.
Figure 5:
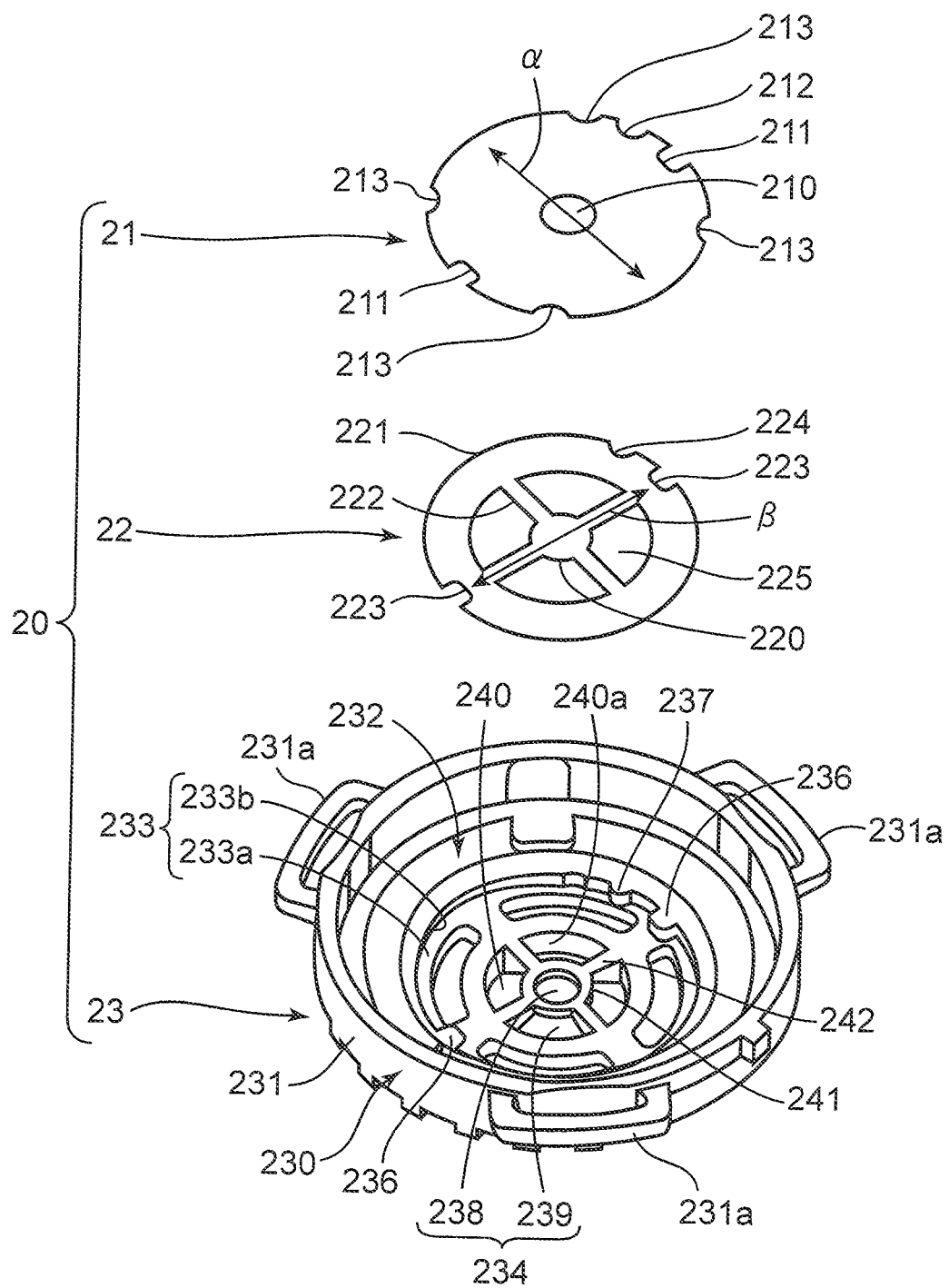
FIG. 5 is an exploded perspective view of the polarization filter unit.
Figure 6:
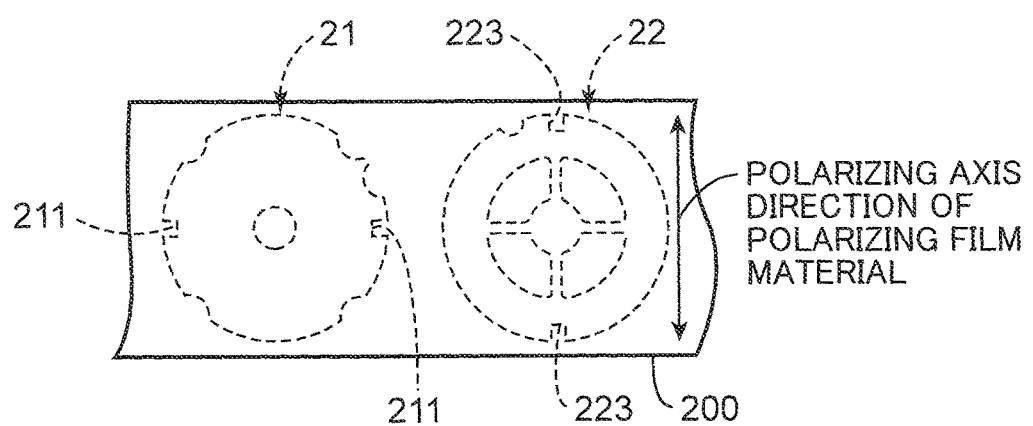
FIG. 6 is an explanatory diagram of a manufacturing method for a set of a first polarization filter and a second polarization filter to be paired with the first polarization filter, of a first type.

FIG. 1 is a perspective view of a color densitometer according to this embodiment, when viewed from an upper side thereof. FIG. 2 is a perspective view of the color densitometer, when viewed from a lower side thereof, wherein a polarization filter unit is detached therefrom. FIG. 3 is a block diagram illustrating a structure of the color densitometer. FIG. 4 is an enlarged explanatory diagram of optical paths of illumination light and reflected light in the vicinity of a polarization filter unit in FIG. 3. FIG. 5 is an exploded perspective view of the polarization filter unit. FIG. 6 is an explanatory diagram of a manufacturing method for a set of a first polarization filter and a second polarization filter to be paired with the first polarization filter, of a first type.

A reflection property measuring device is used for color measurement (including density measurement) for a sample surface, and designed to measure a reflection property of a sample surface, for example, for color evaluation of a printed matter. A reflection property measuring device according to this embodiment will be described as a color densitometer for measuring a print density of ink on a printed matter. For example, as illustrated in FIGS. 1 to 5, a color densitometer 10 as one example of the reflection property measuring device comprises a device main unit 11 and a polarization filter unit 20.

The device main unit 11 comprises a light source 12, an illuminating optical system 13, a light-receiving optical system 14, a light detection section 15, a calculation and control section 16, a display section 17, and a casing 18 housing these components (see FIG. 3). The device main unit 11 is operable to emit illumination light L1 onto a sample surface S through a light-receiving opening 19, and detect a receiving light (reflected light) L2 as the illumination light after being reflected by the sample surface S to thereby measure a reflection property of the sample surface S (in this embodiment, color and density of the sample surface S, e.g., print density of ink on the sample surface S).

The light source 12 is configured to produce light (illumination light) L1 to be emitted onto the sample surface S. For example, the light source 12 in this embodiment is a white LED.

The illuminating optical system 13 is configured to guide the illumination light L1 emitted from the light source 12, to the sample surface S. For example, the illuminating optical system 13 in this embodiment comprises a spherical-shaped first reflecting mirror 131, a second reflecting mirror 132 for changing a traveling direction of the illumination light L1, and a third reflecting mirror 133 for collecting the illumination light L1 on a measurement position of the sample surface S.

The first reflecting mirror 131 is configured to convert the illumination light L1 radially emitted from the light source 12, into parallel light. The first reflecting mirror 131 is formed in a hemispherical shape or a dome shaped obtained by cutting out a part of the hemispherical shape, and the light source 12 is disposed at a center (focal point) thereof. By the first reflecting mirror 131, light emitted from the light source 12 is converted into light (illumination light) L1 having a ring shape when viewed from a light traveling direction (so-called "ring illumination"). The second reflecting mirror 132 is configured to change a traveling direction (propagation direction) of the illumination light L1 from the first reflecting mirror 131 so as to cause the illumination light L1 to be directed toward the sample surface S. The second reflecting mirror 132 in this embodiment is configured to change the direction of the illumination light L1 from the first reflecting mirror 131 so as to cause an optical axis of the illumination light L1 to be aligned with a normal direction to the sample surface S (a normal direction to the light-receiving opening 19). The third reflecting mirror 133 is configured to reduce a diameter of the ring-shaped illumination light L1 from the second reflecting mirror 132 so as to cause the illumination light L1 to be focused on a measurement position of the sample surface S (see FIG. 4). More specifically, the third reflecting mirror 133 is formed in a circular truncated conical cylindrical shape in cross-section along an axial direction thereof (in this embodiment, along a vertical direction). Thus, the third reflecting mirror 133 is operable to reflect the ring-shaped illumination light L1 from the second reflecting mirror 132 so as to cause the illumination light L1 to reach the measurement position in a direction at 45° with respect to a normal direction to the sample surface S (in this embodiment, with respect to a vertical direction). The illumination light L1 after being reflected by the third reflecting mirror 133 is emitted onto the sample surface S through the light-receiving opening 19 of the casing 18.

The light-receiving optical system 14 is configured to guide, as the receiving light L2, an illumination light ray reflected in the normal direction to the sample surface S among illumination light rays reflected by the sample surface S at the measurement position, to the light detection section 15 through the light-receiving opening 19. For example, the light-receiving optical system 14 in this embodiment comprises a field stop 141, a light-receiving lens 142, and an optical fiber 143.

The field stop 141 is configured to restrict entry of light from outside a measurement target area (e.g., reflected light rays from a region of the sample surface S, except the measurement position (see FIG. 4)), into the light-receiving lens 142. The light-receiving lens 142 is configured to collect and enter the receiving light L2 after being passed through the field stop 141, into the optical fiber 143. The optical fiber 143 is configured to guide the receiving light L2 after being collected by the light-receiving lens 142, to the light detection section 15. The light detection section 15 is configured to spectrally disperse the receiving light L2 after being guided by the optical fiber 143, to detect the resulting spectrum, and output the detected spectrum after converting it into an electric signal. The light detection section 15 in this embodiment is a spectrometric device configured to spectrally disperse the receiving light L2 and measure wavelength of each spectral component to thereby detect a spectral distribution of the receiving light L2. The calculation and control section 16 is configured to perform calculation processing based on the electric signal from the light detection section 15, and output a result of the calculation (in this embodiment, a measured print density of ink) to the display section 17. The calculation and control section 16 is also configured to control each component of the device main unit 11 depending on a function of the component. The display section 17 is a display such as a liquid crystal display or an organic EL display, and configured to display the calculation result from the calculation and control section 16.

The polarization filter unit 20 comprises a first polarization filter (illumination light polarizing plate) 21, a second polarization filter (reflected light polarizing plate) 22, and a polarization filter holder (holder) 23. The polarization filter unit 20 in this embodiment is detachably attached to the device main unit 11 (see FIG. 5). Thus, the color densitometer 10 can be used to perform a measurement in a state in which the polarization filter unit 20 is attached thereto, and a measurement in a state in which the polarization filter unit 20 is detached therefrom.

The first polarization filter 21 is inserted into the illuminating optical system 13 to linearly polarize light passed therethrough, in a first polarizing direction (see the arrowed line α in FIG. 5). The first polarization filter 21 has an approximately circular disk shape having an open central region. That is, the first polarization filter 21 has an opening 210 in a central region thereof (central opening). This central opening 210 is a site (region) through which the receiving light L2 is to be passed (see FIG. 4).

The first polarization filter 21 has a plurality of (in this embodiment, two) positioning cutout portions (fitting portions) 211, 211 in an outer peripheral edge region thereof. When the first polarization filter 21 is attached to the polarization filter holder 23, each of the positioning cutout portions 211 can be fitted to a respective one of a plurality of aftermentioned positioning protrusion portions (fittingly-holding portions) 236 of the polarization filter holder 23. By this fitting, a posture of the first polarization filter 21 in the polarization filter holder 23 is set. The positioning cutout portion 211 has a shape fittable to the aftermentioned positioning protrusion portion 236 of the polarization filter holder 23. In this embodiment, it is formed as a cutout concaved radially inwardly toward a central side of the first polarization filter 21 by an appropriate predetermined amount. The two positioning cutout portions 211, 211 in this embodiment are provided, respectively, at opposite ends in a given diametrical direction (in this embodiment, for example, in a direction perpendicular to a polarizing axis (polarizing direction) α) of the first polarization filter 21. That is, the two positioning cutout portions 211, 211 are provided in the outer peripheral edge region of the first polarization filter 21 at respective positions opposed to each other across the central opening 210.

The first polarization filter 21 has a discriminating cutout portion (discriminating portion) 212 for discriminating between an obverse side and a reverse side thereof. The first polarization filter 21 is attached to the polarization filter holder 23, in such a manner as to allow the discriminating cutout portion 212 in this embodiment to be fitted to an aftermentioned discriminating protrusion portion (protruding portion) 237 of the polarization filter holder 23. Thus, when the first polarization filter 21 is attached to the polarization filter holder 23, it is possible to reliably prevent an error in obverse-reverse relationship of the first polarization filter 21 by fitting the discriminating cutout portion 212 to the aftermentioned discriminating protrusion portion 237. The discriminating cutout portion 212 has a shape fittable to the aftermentioned discriminating protrusion portion 237 of the polarization filter holder 23. The discriminating cutout portion 212 in this embodiment is provided in the outer peripheral edge region of the first polarization filter 21, and formed as a cutout (notch) concaved radially inwardly toward the central side of the first polarization filter 21 by an appropriate predetermined amount. In this embodiment, the number of the discriminating cutout portions 212 provided in the first polarization filter 21 is one. Alternatively, a plurality of the discriminating cutout portions 212, 212, - - - may be provided therein.

In the outer peripheral edge region of the first polarization filter 21, four arc-shaped cutout portions 213 are also provided. The arc-shaped cutout portions 213 are provided at respective positions different from those of the two positioning cutout portions 211, 211 and the discriminating cutout portion (discriminating portion) 212, along a circumferential direction of the first polarization filter 21. Each of the cutout portions 213 has a function of indicating an application position of an adhesive for fixing the first polarization filter 21 to the polarization filter holder 23.

The cutout portion 213 also has a function of, when the first and second polarization filters 21, 22 are adhesively bonded to the polarization filter holder 23 in a vertically superposed state, allowing the second polarization filter 22 to ensure an area to be bonded to the adhesive. More specifically, the second polarization filter 22 to be disposed beneath the first polarization filter 21 is configured such that no cutout portion is provided at positions corresponding to the cutout portions 213 (at positions beneath the cutout portions 213). Thus, when the first and second polarization filters 21, 22 are installed to the polarization filter holder 23 in a vertically superposed state, the second polarization filter 22 can be exposed through the cutout portions 213 of the first polarization filter 21. This allows the second polarization filter 22 to, when the adhesive is applied, ensure a bonding area to be bonded to the applied adhesive with a sufficient strength.

The polarization filter holder 23 may be provided with a concave portion serving as an adhesive pool, (specifically, in a peripheral wall surface 233b of an aftermentioned filter installation segment 233) at a site corresponding to each of the cutout portions 213. This concave portion functions as an adhesive pool to strengthen the bonding of the first and second polarization filters 21, 22 to the polarization filter holder 23.

The second polarization filter 22 is inserted into the light-receiving optical system 14 to linearly polarize light passed therethrough, in a second polarizing direction (see the arrowed line β in FIG. 5). A polarizing axis of the second polarization filter 22 intersects orthogonally with the polarizing axis of the first polarization filter 21. That is, the polarizing direction (first polarizing direction α) of the first polarization filter 21 and the polarizing direction (second polarizing direction β) of the second polarization filter 22 mutually intersect orthogonally. The second polarization filter 22 has a filter body 220, an outer circular-ring portion 221, and a plurality of (in this embodiment, four) connection portions 222, 222, - - - each connecting the filter body 220 and the outer circular-ring portion 221. The second polarization filter 22 has a plurality of sector-shaped openings 225 defined by the filter body 220, the outer circular-ring portion 221 and the connection portions 222. In the embodiment illustrated in FIG. 5, the number of the connection portions 222 is four, so that the number of the sector-shaped openings 225 is four.

The filter body 220 is superposed on the central opening 210 the first polarization filter 21 in a direction of superposition of the first polarization filter 21 and the second polarization filter 22 (in FIG. 5, in an up-down (vertical) direction). Specifically, the filter body 220 has a circular disk shape with an outer diameter greater than an inner diameter of the central opening 210, so that it closes the central opening 210, when viewed in the direction of the superposition. That is, the filter body 220 faces the central opening 210.

The outer circular-ring portion 221 has an annular shape in concentric relation to the filter body 220. The outer circular-ring portion 221 has an inner diameter set to form, between the filter body 220 and the outer circular-ring portion 221, a space capable of passing the illumination light L1 therethrough. The outer circular-ring portion 221 has a plurality of (in the embodiment, two) positioning cutout portions 223, 223, in an outer peripheral edge region thereof. When the second polarization filter 22 is attached to the polarization filter holder 23, each of the positioning cutout portions 223 can be fitted to a respective one of the aftermentioned positioning protrusion portions 236 of the polarization filter holder 23. By this fitting, a posture of the second polarization filter 22 in the polarization filter holder 23 is set. That is, in this embodiment, each of the positioning cutout portions 211, 223 of the first polarization filter 21 and the second polarization filter 22 are fitted to a corresponding one of the aftermentioned positioning protrusion portions 236 of the polarization filter holder 23, to thereby allow the first polarization filter 21 and the second polarization filter 22 to be attached to and positioned with respect to the polarization filter holder 23 in respective postures where the polarizing axes (polarizing directions) thereof intersect orthogonally.

Each of the positioning cutout portions 223 has a shape fittable to a respective one of the aftermentioned positioning protrusion portions 236 of the polarization filter holder 23. In this embodiment, it is formed as a cutout (notch) concaved radially inwardly toward a central side of the second polarization filter 22 (toward the filter body 220) by an appropriate predetermined amount. The two positioning cutout portions 223, 223 in this embodiment are provided, respectively, at opposite ends in a given diametrical direction (in this embodiment, for example, in a direction of the polarizing axis (polarizing direction)) of the second polarization filter 22. That is, each of the two positioning cutout portions 223, 223 is formed to have the same shape as that of a respective one of the positioning cutout portions 211 to be aligned with the respective positioning cutout portions 211, and provided at the same position as that of a corresponding one of the positioning cutout portions 211 in the up-down direction. Further, an arrangement direction of the positioning cutout portions 223, 223 of the second polarization filter 22 is coincident with a direction of the polarizing axis of the second polarization filter 22, and an arrangement direction of the positioning cutout portions 211, 211 of the first polarization filter 21 is coincident with a direction perpendicular to the polarizing axis of the first polarization filter 21.

The outer circular ring portion 221 has a discriminating cutout portion (discriminating portion) 224 in the same manner as that in the first polarization filter 21. The second polarization filter 22 is attached to the polarization filter holder 23, in such a manner as to allow the discriminating cutout portion 224 to be fitted to the aftermentioned discriminating protrusion portion (protruding portion) 237 of the polarization filter holder 23. That is, the discriminating cutout portion 224 provided in the outer circular ring portion 221 (second polarization filter 22) is fitted to the aftermentioned discriminating protrusion portion 237 to which the discriminating cutout portion 212 of the first polarization filter 21 is also fitted. Thus, as with the first polarization filter 21, when the first second polarization filter 22 is attached to the polarization filter holder 23, it is possible to reliably prevent an error in obverse-reverse relationship of the second polarization filter 22 by fitting the discriminating cutout portion 224 to the aftermentioned discriminating protrusion portion 237. The discriminating cutout portion 224 has a shape fittable to the aftermentioned discriminating protrusion portion 237 of the polarization filter holder 23. The discriminating cutout portion 224 in this embodiment is formed as a cutout (notch) concaved radially inwardly toward the central side (toward the filter body 220) by an appropriate predetermined amount, as with the first polarization filter 21.

A contour of the outer peripheral edge region of the outer circular ring portion 221 is the same as a contour of the first polarization filter 21, except the four arc-shaped cutout portions 213.

Each of the connection portions 222 extends from the filter body 220 outwardly (in a radially outward direction of the central opening 210) and connects the filter body 220 and the outer circular-ring portion 221. Two sets of the connection portions 222 in this embodiment extend in a direction of the polarizing axis of the second polarization filter 22 (in the second polarizing direction β), and in a direction perpendicular to this polarizing axis, respectively. It should be understood that the number of the connection portions 222 is not limited to four, but may be one to three, or may be five or more. However, from the viewpoint of reliably positioning the filter body 220 with respect to the outer circular-ring portion 221, the number of the connection portions 222 is preferably set to two or more. That is, as long as the space capable of passing the illumination light L1 therethrough can be maintained between the filter body 220 and the outer circular-ring portion 221, and a posture of the filter body 220 with respect to the first polarization filter 21 can be fixed, the number and circumferential positions of the connection portions 222 are not limited.

The set of the first polarization filter 21 and the second polarization filter 22 of a first type configured as above are formed by subjecting a common polarizing film material (polarizing plate material) 200 to punching using two dies (punching dies) each having a shape corresponding to that of a respective one of the polarization filters 21, 22, as illustrated in FIG. 6. Details thereof are as follows. In the following description, the die having a shape corresponding to that of the first polarization filter 21 will be referred to as "first die (first punching die), and the die having a shape corresponding to that of the second polarization filter 22 will be referred to as "second die (second punching die).

One of the dies (e.g., second die) is disposed in a posture where it is rotated 90° with respect to the other die (e.g., first die). For example, in an example illustrated in FIG. 6, the first die is disposed such that the pair of positioning cutout portions 211, 211 are aligned in a longitudinal direction of the polarizing film material 200 (in FIG. 6, in a right-left direction), and the second die is disposed such that the pair of positioning cutout portions 223, 223 are aligned in a width direction of the polarizing film material 200 (in FIG. 6, in an up-down direction). A polarization axis direction of the polarizing film material 200 is coincident with the width direction of the polarizing film material 200 (in FIG. 6, in the up-down direction). It should be understood that respective postures of the first and second dies with respect to the polarizing film material 200 may be reversed, i.e., the first die may be disposed such that the pair of positioning cutout portions 211, 211 are aligned in the width direction of the polarizing film material 200, and the second die may be disposed such that the pair of positioning cutout portions 223, 223 are aligned in the longitudinal direction of the polarizing film material 200. It should also be understood that the posture of the first (second) die with respect to the polarizing film material 200 is not limited to a posture where the arrangement direction of the pair of positioning cutout portions 211, 211 (223, 223) of the punched-out polarization filter 21 (22) is coincident with a direction at 90° or 0° with respect to the width direction (polarizing axis direction) of the polarizing film material 200.

By subjecting the common polarizing film material 200 to punching using the first and second dies arranged in the above manner (through the above punching process), the first polarization filter 21 and the second polarization filter 22 are formed. In this process, by using the first die and the second die, the first polarization filter 21 and the second polarization filter 22 may be punched out simultaneously or may be punched out sequentially one-by-one.

The first polarization filter 21 and the second polarization filter 22 formed in the above manner are paired and attached to the polarization filter holder 23. Thus, even if a manufacturing error occurs in terms of an angle (in this embodiment, 90° or 0°) of the polarizing axis with respect to the arrangement direction of the pair of positioning cutout portions 211, 211 (223, 223), it is possible to ensure adequate accuracy in orthogonality between the two polarizing directions in the attached state to the polarization filter holder 23. That is, in the case where the angle of the polarizing axis with respect to the arrangement direction of the pair of positioning cutout portions 211, 211 (223, 223) is deviated from 90° or 0°, an angular deviation between a direction perpendicular to the polarizing direction and the arrangement direction in the first polarization filter 21 punched out using one of the dies, and an angular deviation between the polarizing direction and the arrangement direction in the second polarization filter 22 punched out using the other die, are the same. Thus, even in such a case, as long as the rotation angle of the second die with respect to the first die is accurately adjusted to become 90°, the polarizing axes of polarization filters 21 accurately intersect orthogonally by pairing the two polarization filters 21, 22 and attaching the pair of polarization filters 21, 22 to the polarization filter holder 23.

In a situation where the first and second polarization filters 21, 22 firmed through a punching process using the pair of dies (first and second dies) are not attached to the polarization filter holder 23 just after completion of the punching process, they are handled (stored) in a paired manner. Then, in an operation for attachment to the polarization filter holder 23, the first and second polarization filters 21, 22 handled in a paired manner are attached to the common polarization filter holder 23. This makes it possible to ensure accuracy in orthogonality between the polarizing directions of the two polarization filters 21, 22 in the state in which they are attached to the polarization filter holder 23.

In this embodiment, the first die and the second die are separate dies. Alternatively, the first die and the second die may be an integrated die. That is, a first die section as a site for punching out the first polarization filter 21 from the polarizing film material 200, and a second die section as a site for punching out the second polarization filter 22 from the polarizing film material 200, may be formed within the same (common) die. In this configuration, a relative posture between the first die section and the second die section is fixed, so that it becomes possible to enhance accuracy in orthogonality between the two die sections, as compared to the case where the first die and the second die are formed as separate dies as in this embodiment, thereby ensuring adequate accuracy in orthogonality between the polarizing directions of the first and second polarization filters 21, 22 punched out using the integrated die. It also becomes possible to reduce a manufacturing cost of the die, as compared to the case where the first die section and the second die section are formed as separate dies. Further, it becomes possible to facilitate an attaching operation necessary when the first die section and the second die section are attached, for example, to an apparatus for punching out the first polarization filter 21 and the second polarization filter 22 from the polarizing film material 200.

In this case (the case where the first die section and the second die section are formed as an integral die, the first die section and the second die section may have a configuration capable of punching out the first polarization filter 21 and the second polarization filter 22 from the polarizing film material 200, in a mutually connected state. The first polarization filter 21 and the second polarization filter 22 punched out in a mutually connected state are separated from each other before the operation of attaching them to the polarization filter holder 23. This makes it possible to facilitate handling the first polarization filter 21 and the second polarization filter 22 as a pair after the punching process, and more reliably prevent a situation where the first polarization filter 21 and the second polarization filter 22 each selected from a respective one of two different pairs are attached to the polarization filter holder 23, thereby causing deteriorated accuracy in orthogonality between the polarizing directions of the two polarization filters 21, 22.

The polarization filter holder 23 is configured to hold the first polarization filter 21 and the second polarization filter 22 in a mutually superposed state in a thickness direction of each of the polarizing filters 21, 22. That is, the first polarization filter 21 and the second polarization filter 22 are attached to the polarization filter holder 23 in a mutually superposed state. The polarization filter holder 23 in this embodiment holds the first polarization filter 21 and the second polarization filter 22 in such a manner that the first polarization filter 21 is located on a relatively upper side, and the second polarization filter 22 is located on a relatively lower side. Alternatively, the relationship of the superposition may be reversed.

The polarization filter holder 23 is configured to be detachable to the device main unit 11. The polarization filter holder 23 in this embodiment is detachably attached to the device main unit 11 by means of a bayonet structure. Returning to FIG. 5, the polarization filter holder 23 has a holder body 230 to which the first polarization filter 21 and the second polarization filter 22 can be attached, and a plurality of holder fixing protrusions 231a, 231a, - - - provided on an outer peripheral surface of the holder body 239 to protrude radially outwardly. The polarization filter holder 23 can be locked to the device main unit 11 by inserting each of the holder fixing protrusions 231a into a respective one of a plurality of cutout portions 19a provided around the light-receiving opening 19 of the device main unit 11 (see FIG. 2) and, in this state, turning the holder body 230 in a circumferential direction thereof. When it is necessary to detach the polarization filter holder 23 from the device main unit 11, an operation reverse to the above operation is performed, so that the polarization filter holder 23 can be detached from the device main unit 11.

The holder body 230 has a short cylindrical-shaped peripheral wall 231 provided with the holder fixing protrusions 231a, and a bottom 232 provided at a lower end of the peripheral wall portion 231. The bottom 232 has a filter installation segment 233 formed by concaving a central region thereof downwardly with respect to a region surrounding the central region, and a light passing segment 234 provided in a central portion of the filter installation segment 233 and configured to pass the illumination light L1 and the receiving light L2 therethrough.

The filter installation segment 233 has a plurality of positioning protrusion portions (fittingly-holding portions) 236 for setting respective held postures of the first polarization filter 21 and the second polarization filter 22 in the polarization filter holder 23, and a discriminating protrusion portion 237 (protruding portion) for use in discriminating between the obverse and reverse surfaces of each of the first polarization filter 21 and the second polarization filter 22. More specifically, the filter installation segment 233 has a loading surface 233a on which the first polarization filter 21 and the second polarization filter 22 are to be placed in a mutually superposed state, and a peripheral wall surface 233b circumferentially surrounding the first polarization filter 21 and the second polarization filter 22 placed on the loading surface 233a. The filter installation segment 233 has a plurality of positioning protrusion portions 236 at positions corresponding to the positioning cutout portions 211 223 of the polarization filter 21 22 to protrude upwardly from the loading surface 233a and protrude radially inwardly from the peripheral wall surface 233b. The filter installation segment 233 has a discriminating protrusion portion 237 at a position corresponding to the discriminating cutout portion 212 224 of the polarization filter 21 22 to protrude upwardly from the loading surface 233a and protrude radially inwardly from the peripheral wall surface 233b.

Each of the positioning protrusion portions 236 has a shape compatible with (fittable to) a respective one of the positioning cutout portions 211 223 of the polarization filter 21 22. The discriminating protrusion portion 237 has a shape corresponding to (fittable to) the discriminating cutout portion 212 224 of the polarization filter 21 22.

The light passing segment 234 has a receiving-light passing portion 238 configured to pass the receiving light L2 therethrough, and a plurality of illumination-light passing sections 239 each provided around the receiving-light passing portion 238 to pass the illumination light L1 therethrough. More specifically, the light passing segment 234 has: a circular-shaped opening 240 provided in a central region of the loading surface 233a; an annular-shaped member 241 provided within the circular-shaped opening 240 to have an outer diameter less than a diameter of the circular-shaped opening 240; and a plurality of support portions (light blocking portions) 242, 242, - - - connecting an inner peripheral surface 240a defining the circular-shaped opening 240 and the annular-shaped member 241 to support the annular-shaped member 241 within the circular-shaped opening 240. The receiving-light passing portion 238 is an opening inside the annular-shaped member 241, and each of the illumination-light passing sections 239 is an opening surrounded by the inner peripheral surface 240a defining the circular-shaped opening 240, two adjacent ones of the support portions 242, and the annular-shaped member 241. The sector-shaped opening 225 of the second polarization filter 22 has a size equal to or slightly greater than a size of the illumination-light passing section 239.

The annular-shaped member 241 has an inner diameter equal to or slightly less than the diameter of the central opening 210 of the first polarization filter 21. The outer diameter of the annular-shaped member 241 is equal to or slightly greater than the diameter of the filter body 220 of the second polarization filter 22. The diameter of the inner peripheral surface 240a defining the circular-shaped opening 240 equal to or slightly less than the inner diameter of the outer circular-ring portion 221 of the second polarization filter 22. Each of the support portions 242 is formed to extend along a respective one of the connection portions 222 of the second polarization filter 22, and disposed in side-by-side relation to and beneath the connection portion 222. The support portion 242 has a width equal to or slightly greater than a width of the connection portion 222.

In the above color densitometer 10, when the two polarization filters (the first polarization filter 21 and the second polarization filter 22) are attached to (held by) the polarization filter holder 23, it is possible to establish orthogonality between the polarizing axes of the two polarization filters 21, 22 accurately (i.e., according to component processing accuracy) and easily by a simple operation consisting only of fittingly attaching each of the positioning cutout portions 211 223 to a corresponding one of the positioning protrusion portions 236. Thus, the color densitometer 10 can accurately measure a reflection property of (in this embodiment, a print density of ink on) the sample surface S, while eliminating an influence of dry-down.

In the color densitometer 10 according to this embodiment, the first polarization filter 21 is formed in a shape capable of avoiding (shape free from blocking) an optical path of the receiving light L2, and the second polarization filter 22 is formed in a shape capable of avoiding (shape free from blocking) an optical path of the illumination light L1. Thus, even when the first polarization filter 21 and the second polarization filter 22 are inserted in both of the illuminating optical system 13 and the light-receiving optical system 14, while being mutually superposed in such a manner as to allow the respective polarizing axes thereof to intersect orthogonally, it becomes possible to ensure passing of the illumination light L1 at an installation position of the second polarization filter 22 in the illuminating optical system 13 and passing of the receiving light L2 at an installation position of the first polarization filter 21 in the light-receiving optical system 14. This allows the illuminating optical system 13 and the light-receiving optical system 14 to be arranged in adjacent relation to each other to thereby achieve a reduction in size of the color densitometer 10. In addition, even when the color densitometer 10 is configured such that the illuminating optical system 13 and the light-receiving optical system 14 are arranged in adjacent relation to each other, a size of each of the polarization filters 21, 22 can be ensured (i.e., each of the polarization filters 21, 22 can be increased in size) by forming each of the polarization filters 21, 22 to have a size extending across both of the illuminating optical system 13 and the light-receiving optical system 14. This makes it possible to maintain easiness of the operation of attaching the polarization filters 21, 22 to the polarization filter holder 23 in such a manner as to allow the polarizing axes thereof to intersect orthogonally.

In the color densitometer 10 according to this embodiment, when the first polarization filter 21 and the second polarization filter 22 are installed, a configuration capable of establishing orthogonality between the polarizing axes thereof in an accurate and easy manner is realized by a simple mechanism comprising the positioning protrusion portions 236 each protruding in the direction of the superposition of the two polarization filters 21, 22, and the cutouts (the positioning cutout portions 211, 223) each having a shape compatible with a respective one of the positioning protrusion portions 236.

Each of the polarization filters 21, 22 is provided with a respective one of the discriminating cutout portions 212, 224, so that it becomes possible to discriminate between an obverse side and a reverse side of each of the polarization filters 21, 22 in an easy and reliable manner. Thus, when the polarization filters 21, 22 are attached to the polarization filter holder 23, it becomes possible to prevent erroneous attachment in terms of an obverse-reverse relationship, in an easy and reliable manner.

Further, the color densitometer 10 according to this embodiment is configured such that the cutout (discriminating cutout portions 212, 224 each provided in a respective one of the polarization filters 21, 22 are fitted to the discriminating protrusion portion 237 of the polarization filter holder 23 (in other words, the polarization filters 21, 22 can be attached to the polarization filter holder 23 only if the discriminating cutout portions 212, 224 each provided in a respective one of the polarization filters 21, 22 are fitted to the discriminating protrusion portion 237 of the polarization filter holder 23), thereby more reliably preventing an error in the obverse-reverse relationship during the operation of attaching the polarization filters 21, 22 to the polarization filter holder 23.

In the color densitometer 10 according to this embodiment, one of the positioning cutout portions 211 of the first polarization filter 21 and one of the positioning cutout portions 223 of the second polarization filter 22 corresponding to the one positioning cutout portion 211 are fitted to the same (common) one of the positioning protrusion portions 236 of the polarization filter holder 23. Thus, it becomes possible to more accurately establish orthogonality between the polarizing axes, as compared to a configuration in which they are fitted, respectively, to two protrusions provided at different positions.

In the color densitometer 10 according to this embodiment, each of the positioning cutout portions 211, 233 is located outside a region through which the illumination light L1 and the receiving light L2 are to be passed. Thus, even if a manufacturing error occurs in terms of a shape of the positioning protrusion portions 236 or the positioning cutout portions 211, 223, it becomes possible to suppress an influence on accuracy in orthogonality between the polarizing directions of the two polarization filters 21, 22. That is, each of the positioning protrusion portions 236 and the positioning cutout portions 211, 233 is provided outside a region through which the illumination light L1 and the receiving light L2 are to be passed (i.e., at a position away from a central region of each of the first polarization filter 21 and the second polarization filter 22), so that, as compared to the case where it is provided within the region through which the illumination light L1 and the receiving light L2 are to be passed (i.e., in the central region of each of the first polarization filter 21 and the second polarization filter 22), it becomes possible to suppress a circumferential deviation which would otherwise occur when the polarization filters 21, 22 are attached to the polarization filter holder 23. Thus, the color densitometer 10 according to this embodiment can suppress an influence on accuracy in orthogonality between the polarizing directions of the two polarization filters 21, 22.

In the color densitometer 10 according to this embodiment, the polarization filter holder 23 has the support portions 242 each disposed in side-by-side relation to a respective one of the connection portions 222 of the second polarization filter 22 in the direction of the superposition of the two polarization filters 21, 22, so that it becomes possible to suppress an influence of the connection portions 222 each disposed at a position across the optical path of the ring-shaped illumination light L1 (specifically, the connection portions 222 as a part of the second polarization filter 22 whose polarizing axis interests orthogonally with the polarizing axis of the first polarization filter 21). Therefore, the color densitometer 10 according to this embodiment can accurately measure a reflection property of (in this embodiment, a print density of ink on) the sample surface S.

It should be understood that the reflection property measuring device and the method of manufacturing polarizing plates for use in the reflection property measuring device, of the present invention, are not limited to the above embodiment, but various changes and modifications may be made therein without departing from the spirit and scope of the present invention as set forth in appended claims.

The reflection property measuring device is not limited to a color densitometer. That is, the reflection property measuring device may be a device for performing a color measurement, such as a device for performing measurement of another reflection property of the sample surface, such as color values.

Figure 7A:
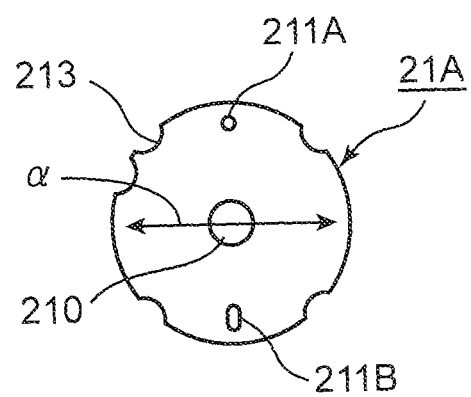
FIG. 7 illustrates top plan views of a set of a first polarization filter, and a second polarization filter to be paired with the first polarization filter, of a second type.
Figure 7B:
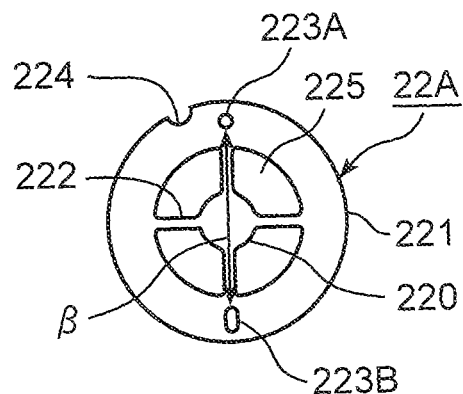
Figure 8A:
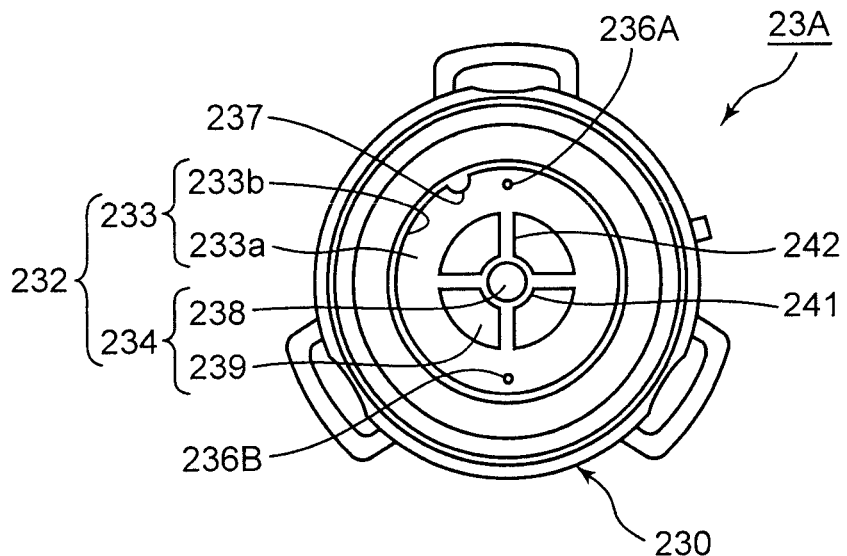
FIG. 8 illustrates top plan views of a polarization filter holder and a polarization filter unit, in the second type.
Figure 8B:
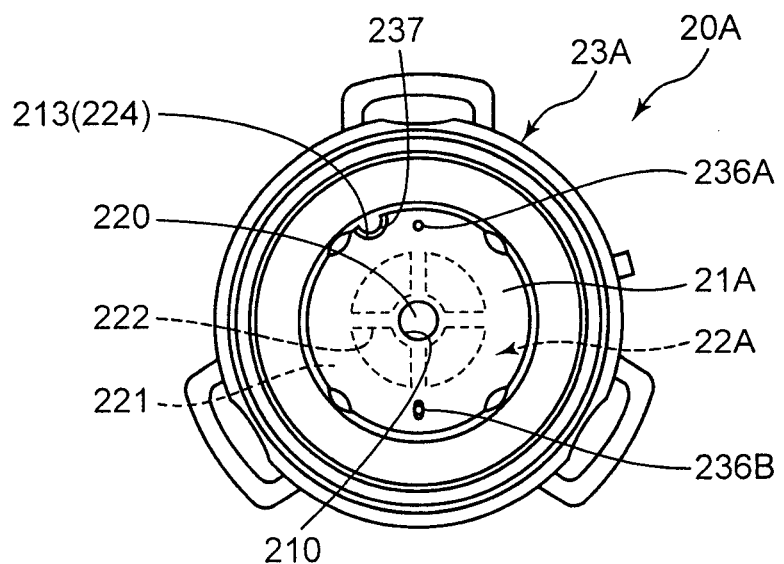
Figure 9A:
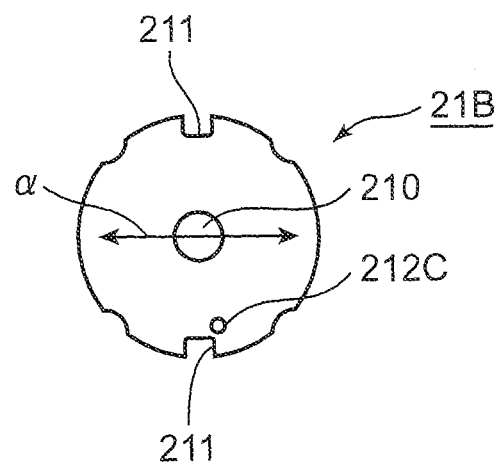
FIG. 9 illustrates top plan views of a set of a first polarization filter and a second polarization filter to be paired with the first polarization filter, of a third type.
Figure 9B:
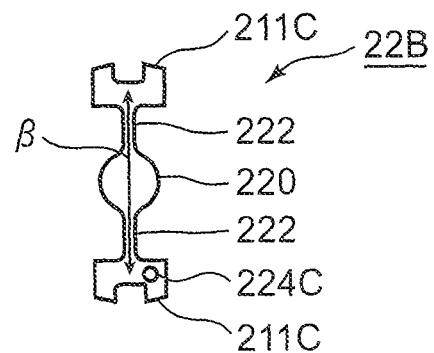
Figure 10A:
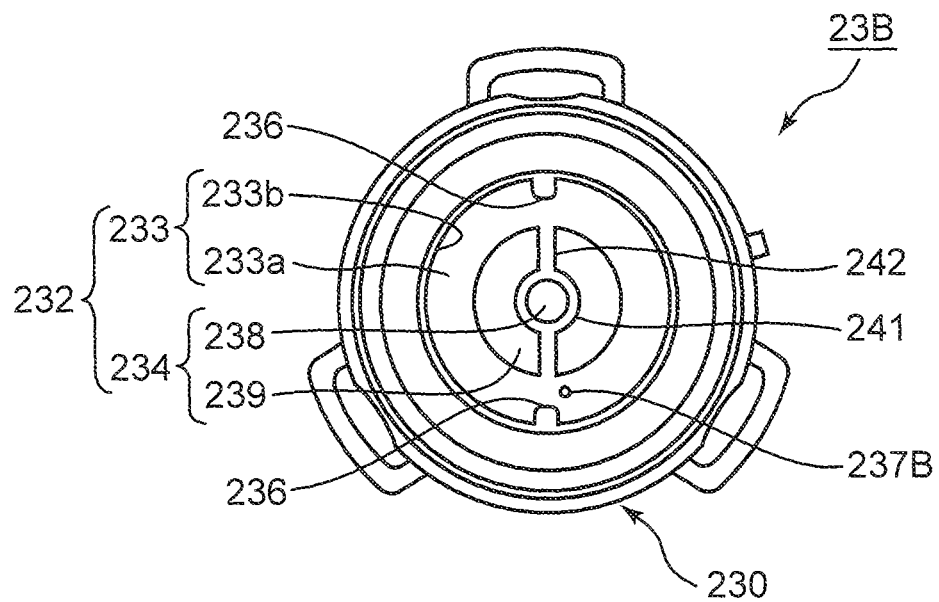
FIG. 10 illustrates top plan views of a polarization filter holder and a polarization filter unit, in the third type.
Figure 10B:
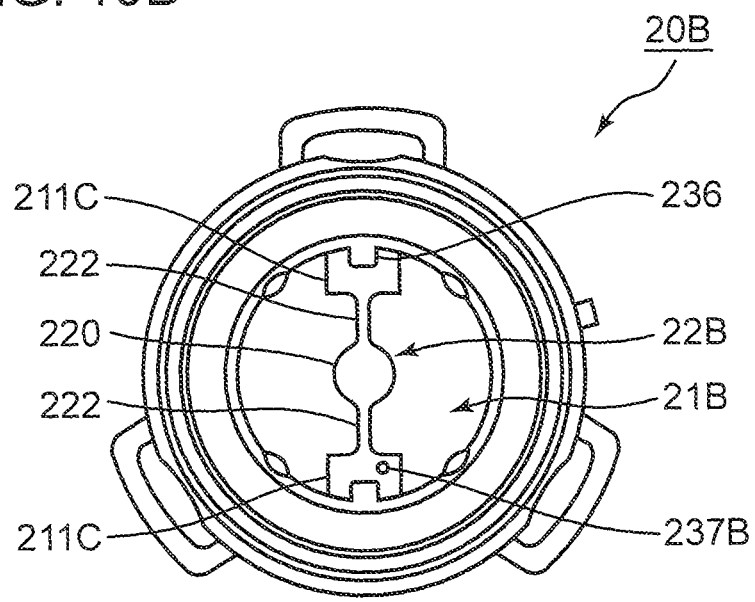
Figure 11:
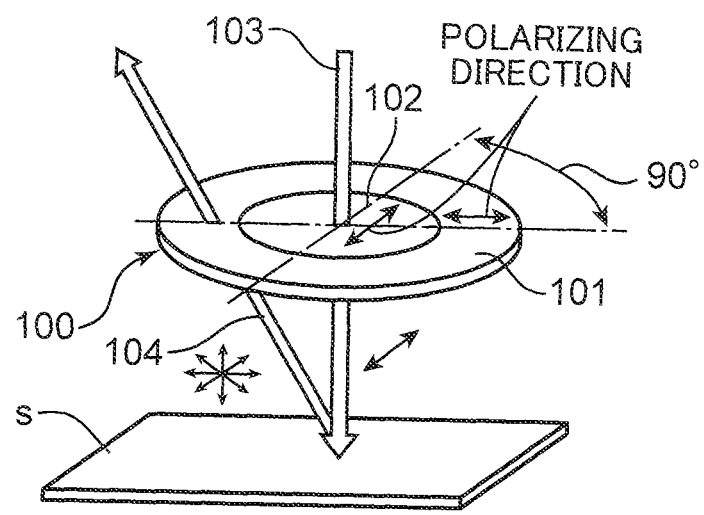
FIG. 11 is an explanatory diagram of a conventional polarization filter.

FIG. 7 illustrates top plan views of a set of a first polarization filter and a second polarization filter to be paired with the first polarization filter, of a second type. FIG. 7A is a top plan view of the first polarization filter in the second type, and FIG. 7B is a top plan view of the second polarization filter in the second type. FIG. 8 illustrates top plan views of a polarization filter holder and a polarization filter unit, in the second type. FIG. 8A is a top plan view of the polarization filter holder in the second type, and FIG. 8B is a top plan view of the polarization filter unit in the second type. FIG. 9 illustrates top plan views of a set of a first polarization filter and a second polarization filter to be paired with the first polarization filter, of a third type. FIG. 9A is a top plan view of the first polarization filter in the third type, and FIG. 9B is a top plan view of the second polarization filter in the third type. FIG. 10 illustrates top plan views of a polarization filter holder and a polarization filter unit, in the third type. FIG. 10A is a top plan view of the polarization filter holder in the third type, and FIG. 10B is a top plan view of the polarization filter unit in the third type.

In the color densitometer 10 according to this embodiment, a fitting site between the polarization filter holder 23 and a fitting site of the polarization filter 21 22 is composed of the protrusion (positioning protrusion portion) 236 and the cutout (positioning cutout portion) 211 223 having a shape compatible with the protrusion 236. However, the present invention is not limited thereto. For example, the protrusion may be provided as a fitting portion of each of the polarization filters, and the cutout or concave portion having a shape compatible with (fittable to) the protrusion may be provided as a fittingly-holding portion of the polarization filter holder. Further, as illustrated in FIGS. 7A to 8B, a polarization filter holder 23A may be provided with a pair of protrusions (positioning protrusion portions) 236A, 236B, and a polarization filter 21A 22A may be provided with a pair of holes (positioning holes) 211A, 211B 223A, 223B each having a shape compatible with (fittable to) a respective one of the protrusions 236A, 236B. In this case, it is preferable that one 211B 223B of the positioning holes 211A, 211B (223A, 223B) aligned in a diametrical direction is formed to become longer in the diametrical direction (in a direction along which the pair of positioning holes 211A, 211B (223A, 223B) are aligned) than the positioning protrusion portion 236B to be inserted into the positioning hole 211B (223B). This configuration makes it possible to absorb machining errors of the positioning holes 211A, 211B 223A, 223B provided in the polarization filter 21A 22A and the positioning protrusion portions 236A, 236B provided in the polarization filter holder 23A.

Further, a discriminating portion provided in the polarization filter 21A (22B) to discriminate between an obverse side and a reverse side thereof is not limited to a cutout, but may be a hole (discriminating hole) 212C (224C) (see FIGS. 9A to 10B) or the like. In this case, a polarization filter holder 23B is provided with a discriminating protrusion portion 237B having a shape compatible with the discriminating hole 212C (224C). The discriminating protrusion portion 237B protrudes upwardly of a loading surface 233a.

Further, the discriminating portion for discriminating between the obverse side and the reverse side may be provided only in each of the polarization filters. In this case, it also becomes possible to prevent erroneous attachment in terms of an obverse-reverse relationship, for example, by visually checking the discriminating portion during the operation of attaching each of the polarization filters to the polarization filter holder. Instead of a structural shape such as a cutout or a hole, the discriminating portion provided in each of the polarization filters may be composed of a mark, character or the like formed by stamping, printing or the like.

Further, as illustrated in FIGS. 9 to 10B, the second polarization filter 22B may have a configuration devoid of the outer circular-ring portion. That is, the second polarization filter 22B may have: a filter body 220; a fitting portion 211C fittable to a fittingly-holding portion (e.g., protrusion) of the polarization filter holder 23B; and a connection portion 222 connecting the filter body 220 and the fitting portion 211C (see FIG. 9B). In this case, a support portion (supporting an annular-shaped member 241) of the second polarization filter 22B may be provided only at a position where it is superposed on the connection portion 222 in a direction of superposition of the polarization filters 21B, 22B.

In the color densitometer 10 according to this embodiment, the two polarization filters 21, 22 are placed on the loading surface 233a of the filter installation segment 233 of the polarization filter holder 23 in a mutually superposed state. However, the present invention is not limited to this arrangement. For example, the first polarization filter 21 and the second polarization filter 22 are attached, respectively, to an upper surface and a lower surface of the polarization filter holder 23, in such a manner that the first and second polarization filters 21, 22 are mutually superposed, while sandwiching the polarization filter holder 23 (filter installation segment 233) therebetween. In this case, the positioning protrusion portions (fittingly-holding portions) are provided on each of the upper surface and the lower surface of the polarization filter holder 23.

Even in the case where the polarization filters 21, 22 are installed in the above manner, the polarization filter holder 23 may be provided with a fittingly-holding portion (e.g., the positioning protrusion portion), and each of the polarization filters 21, 22 may be provided with a fitting portion (e.g., the positioning cutout portion). Thus, when the first polarization filter 21 and the second polarization filter 22 are installed to the polarization filter holder 23, it becomes possible to establish orthogonality between the polarizing directions thereof in an accurate and easy manner.

In the color densitometer 10 according to this embodiment, the ring illumination capable of illuminating a measurement position of the sample surface S from the entire circumference is employed. Alternatively, unidirectional illumination in which illumination light is emitted in one direction, bidirectional illumination in which illumination light is emitted in two directions, or multi-directional illumination in which illumination light is emitted from a plurality of positions on a circle surrounding a normal line to the sample surface S (in a plurality of directions from points equally spaced on the circle (equidistance directions)) to a position of an intersection point between the normal line and the sample surface S may be employed.

As mentioned above, this specification discloses techniques of various types. Among them, major techniques will be outlined below.

According to one aspect, there is provided a reflection property measuring device for measuring a reflection property of a sample surface by emitting illumination light onto the sample surface and detecting reflected light as the illumination light after being reflected by the sample surface. The reflection property measuring device comprises: an illumination light polarizing plate inserted in an illuminating optical system for guiding the illumination light to the sample surface, and configured to linearly polarize light passed therethrough, in a first polarizing direction; a reflected light polarizing plate inserted in a light-receiving optical system for guiding the reflected light to a light detection section, and configured to linearly polarize light passed therethrough, in a second polarizing direction; and a holder holding the illumination light polarizing plate and the reflected light polarizing plate in a mutually superposed state in a thickness direction of each of the polarizing plates. The holder has one or more fittingly-holding portions for setting respective held postures of the illumination light polarizing plate and the reflected light polarizing plate in the holder. The illumination light polarizing plate has one or more fitting portions each fittable to a corresponding one of the fittingly-holding portions of the holder, wherein the illumination light polarizing plate is formed in a shape capable of avoiding an optical path of the reflected light. The reflected light polarizing plate has one or more fitting portions each fittable to a corresponding one of the fittingly-holding portions of the holder, wherein the reflected light polarizing plate is formed in a shape capable of avoiding an optical path of the illumination light. The fitting portions are provided at positions where they are fitted, respectively, to the corresponding fittingly-holding portions to thereby allow the illumination light polarizing plate and the reflected light polarizing plate to be held by the holder in respective postures where polarizing directions thereof intersect orthogonally.

In the above reflection property measuring device, when the two polarizing plates (the illumination light polarizing plate and the reflected light polarizing plate) are attached to (held by) the holder, it is possible to establish orthogonality between the polarizing directions of the two polarizing plates accurately (i.e., according to component processing accuracy) and easily by a simple operation consisting only of fittingly attaching each of the fitting portions to a corresponding one of the fittingly-holding portions.

In the above reflection property measuring device, the illumination light polarizing plate is formed in a shape capable of avoiding an optical path of the reflected light, and the reflected light polarizing plate is formed in a shape capable of avoiding an optical path of the illumination light. Thus, even when the illumination light polarizing plate and the reflected light polarizing plate are inserted in both of the illuminating optical system and the light-receiving optical system, while being mutually superposed in such a manner as to allow the respective polarizing directions thereof to intersect orthogonally, it becomes possible to ensure passing of the illumination light at an installation position of the reflected light polarizing plate in the illuminating optical system and passing of the reflected light at an installation position of the illumination light polarizing plate in the light-receiving optical system. Thus, in the above reflection property measuring device, the illuminating optical system and the light-receiving optical system can be arranged in adjacent relation to each other to thereby achieve a reduction in size of the reflection property measuring device. In addition, even when the reflection property measuring device is configured such that the illuminating optical system and the light-receiving optical system are arranged in adjacent relation to each other, a size of each of the polarizing plates (the illumination light polarizing plate and the reflected light polarizing plate) can be ensured by forming each of the polarizing plates to have a size allowing for insertion into both of the illuminating optical system and the light-receiving optical system. This makes it possible to maintain easiness of an operation of attaching the polarizing plates to the holder in such a manner as to allow the polarizing directions thereof to intersect orthogonally.

Preferably, in the above reflection property measuring device, each of the fittingly-holding portions of the holder protrudes in a direction of superposition of the illumination light polarizing plate and the reflected light polarizing plate, and each of the fitting portions is a hole or a cutout fittable to the corresponding one of the fittingly-holding portions. In this embodiment, when the illumination light polarizing plate and the reflected light polarizing plate are installed, a configuration capable of establishing orthogonality between the polarizing directions thereof in an accurate and easy manner is realized by a simple mechanism comprising the fittingly-holding portion protruding in the direction of the superposition, and a hole or cutout having a shape compatible with the fittingly-holding portion.

Preferably, in the above reflection property measuring devices, each of the illumination light polarizing plate and the reflected light polarizing plate has a discriminating portion for discriminating between an obverse side and a reverse side thereof.

Each of the polarizing plates (the illumination light polarizing plate and the reflected light polarizing plate) is provided with the discriminating cutout portion, so that it becomes possible to discriminate between an obverse side and a reverse side of each of the polarizing plates in an easy and reliable manner. Thus, in the reflection property measuring device according to this embodiment, when the polarizing plates are attached to the holder, it becomes possible to prevent erroneous attachment in terms of an obverse-reverse relationship, in an easy and reliable manner.

Preferably, in the above reflection property measuring device, the holder has a protruding portion protruding in a direction of superposition of the illumination light polarizing plate and the reflected light polarizing plate, and the discriminating portion is a hole or a cutout provided in each of the illumination light polarizing plate and the reflected light polarizing plate at a position corresponding to the protruding portion, and configured to be fittable to the protruding portion.

The reflection property measuring device is configured such that a hole or cutout provided in each of the polarizing plates is fitted to the protruding portion of the holder (in other words, each of the polarizing plates can be attached to the holder only if a hole or cutout provided in each of the polarizing plates is fitted to the protruding portion of the holder), thereby more reliably preventing an error in the obverse-reverse relationship during the operation of attaching the polarizing plates to the holder.

Preferably, in the above reflection property measuring devices, one of the fitting portions of the illumination light polarizing plate, and one of the fitting portions of the reflected light polarizing plate corresponding to the one fitting portion of the illumination light polarizing plate, are fitted to a common one of the fittingly-holding portions of the holder.

In the reflection property measuring device, it becomes possible to reliably fittingly hold the fitting portion of the illumination light polarizing plate and the fitting portion of the reflected light polarizing plate by the corresponding fittingly-holding portion, thereby more reliably establishing orthogonality between the polarizing directions of the illumination light polarizing plate and the reflected light polarizing plate. That is, in a configuration in which the fitting portion of the illumination light polarizing plate and the fitting portion of the reflected light polarizing plate are fitted, respectively, to different fittingly-folding portions of the folder, a relatively large number of fittingly-folding portions are provided in the holder, so that erroneous fitting is liable to occur. In contrast, the above configuration makes it possible to reduce the number of the fittingly-folding portions. Thus, the reflection property measuring device according to this embodiment can effectively prevent the erroneous fitting.

In the above reflection property measuring device, the holder may hold the illumination light polarizing plate and the reflected light polarizing plate, in such a manner that the illumination light polarizing plate and the reflected light polarizing plate are mutually superposed, while sandwiching the holder therebetween.

Even in the case where the illumination light polarizing plate and the reflected light polarizing plate are installed in such a manner that the holder is sandwiched between the illumination light polarizing plate and the reflected light polarizing plate, the holder may be provided with a fittingly-holding portion, and each of the polarizing plates may be provided with a fitting portion compatible with the fittingly-holding portion. Thus, when the illumination light polarizing plate and the reflected light polarizing plate are installed to the holder, the reflection property measuring device according to this embodiment can establish orthogonality between the polarizing directions thereof in an accurate and easy manner.

Preferably, in the above reflection property measuring devices, the reflected light is passed through a central portion of each of the illumination light polarizing plate and the reflected light polarizing plate, whereas the illumination light is passed around the reflected light, or the illumination light is passed through the central portion, whereas the reflected light is passed around the illumination light, wherein each of the fitting portions of the illumination light polarizing plate and the reflected light polarizing plate is located outside a region through which the illumination light and the reflected light are to be passed.

In the reflection property measuring device, even if a manufacturing error occurs in terms of a shape of the fittingly-holding portion or the fitting portion, it becomes possible to suppress an influence on accuracy in orthogonality between the polarizing directions of the two polarizing plates (the illumination light polarizing plate and the reflected light polarizing plate). That is, each of the fittingly-holding portion and the fitting portion is provided outside a region through which the illumination light and the reflected light are to be passed (i.e., at a position away from a central region of each of the illumination light polarizing plate and the reflected light polarizing plate), so that, as compared to the case where it is provided within the region through which the illumination light and the reflected light are to be passed (i.e., in the central region of each of the illumination light polarizing plate and the reflected light polarizing plate), it becomes possible to suppress a circumferential deviation which would otherwise occur when the polarizing plates are attached to the holder. Thus, the reflection property measuring device according to this embodiment can suppress an influence on accuracy in orthogonality between the polarizing directions of the two polarizing plates.

In the above reflection property measuring devices, the illuminating optical system may be configured to guide the illumination light to the sample surface, in such a manner that the illumination light has a ring shape at a position of the illumination light polarizing plate, and the light-receiving optical system may be configured to guide the reflected light to the light detection section, in such a manner that a part of the illumination light after being reflected by the sample surface is passed through a central region of the ring-shaped illumination light at the position of the illumination light polarizing plate, to serve as the reflected light. In this case, for example, the illumination light polarizing plate may have an opening formed in a central portion thereof to pass the reflected light therethrough, and the reflected light polarizing plate may have a plate body superposed on the opening of the illumination light polarizing plate in the direction of the superposition with the illumination light polarizing plate, the fitting portions provided outside a region which surrounds the plate body and through which the ring-shaped illumination light is to be passed, and a connection portion extending from the plate body to the fitting portions. This makes it possible to eliminate an influence of dry-down to thereby accurately measure the reflection property of the sample surface.

In this configuration, the ring-shaped illumination light reaches the sample surface after being passed around the plate body of the reflected light polarizing plate. Then, the illumination light after being reflected by the sample surface and passed through the opening in the central portion of the illumination light polarizing plate is guided as the reflected light to the light detection section.

Preferably, in the above reflection property measuring device, the holder has a light blocking portion formed to extend along the connection portion of the reflected light polarizing plate and disposed in side-by-side relation to the connection portion in the direction of the superposition.

The reflection property measuring device can suppress an influence of the connection portion disposed at a position across the optical path of the ring-shaped illumination light (specifically, the connection portion as a part of the reflected light polarizing plate whose polarizing direction interests orthogonally with the polarizing direction of the illumination light polarizing plate), thereby accurately measuring the reflection property of the sample surface.

According to another aspect, there is provided a method of manufacturing an illumination light polarizing plate and a reflected light polarizing plate for use in a reflection property measuring device for measuring a reflection property of a sample surface by emitting illumination light onto the sample surface and detecting reflected light as the illumination light after being reflected by the sample surface, wherein the illumination light polarizing plate and the reflected light polarizing plate are held by a holder in respective postures where polarizing directions thereof intersect orthogonally. The method comprises a punching step of punching out the illumination light polarizing plate and the reflected light polarizing plate from a same polarizing plate material by using a first die having a shape corresponding to that of the illumination light polarizing plate, and a second die having a shape corresponding to that of the reflected light polarizing plate, wherein the first die and the second die are arranged such that an arrangement direction of a pair of first fitting portions and an arrangement direction of a pair of second fitting portions mutually intersect orthogonally, wherein: in a state after the illumination light polarizing plate is punched out from the polarizing plate material by using the first die, the first fitting portions are provided in an outer peripheral edge portion of the illumination light polarizing plate at positions opposed to each other across a center of the illumination light polarizing plate, and fittable, respectively, to a pair of fittingly-holding portions provided in the holder at positions corresponding to the first fitting portions; and, in a state after the reflected light polarizing plate is punched out from the polarizing plate material by using the second die, the second fitting portions are provided in an outer peripheral edge portion of the reflected light polarizing plate at positions opposed to each other across a center of the reflected light polarizing plate and corresponding to the respective first fitting portions of the illumination light polarizing plate, and wherein each of the second fitting portions has the same shape as that of a respective one of the first fitting portions.

The illumination light polarizing plate and the reflected light polarizing plate formed by subjecting the polarizing plate material to punching using the first die and the second die arranged in the above manner are paired and attached to the holder. Thus, when the illumination light polarizing plate and the reflected light polarizing plate are attached to the holder in such a manner that each of the fitting portions of the illumination light polarizing plate and a corresponding one of the fitting portions of the reflected light polarizing plate are fitted to a common one of the fittingly-holding portions of the holder, it becomes possible to ensure adequate accuracy in orthogonality between the polarizing directions thereof.

In the above method, the first die and the second die may be formed as an integrated die, wherein the punching step may include simultaneously punching out the illumination light polarizing plate and the reflected light polarizing plate from the polarizing plate material by using the integrated die.

In the method according to this embodiment, a relative posture between the first die and the second die is fixed in the integrated die (that is, they are fixed in respective postures where the arrangement direction of the pair of first fitting portions and the arrangement direction of the pair of second fitting portions intersect orthogonally). Thus, it becomes possible to enhance accuracy in orthogonality between the two dies, as compared to the case where the first die and the second die are formed as separate dies, thereby ensuring adequate accuracy in orthogonality between the polarizing directions of the illumination light polarizing plate and the reflected light polarizing plate punched out using the integrated die. It also becomes possible to reduce a manufacturing cost of the die, as compared to the case where the first die and the second die are formed as separate dies. Further, it becomes possible to facilitate an attaching operation necessary when the first die and the second die are attached, for example, to an apparatus for punching out the illumination light polarizing plate and the reflected light polarizing plate from the polarizing film material.

In the above method, the first die and the second die in the integrated die may have a configuration capable of punching out the illumination light polarizing plate and the reflected light polarizing plate from the polarizing plate material, in a mutually connected state.

This makes it possible to facilitate handling the illumination light polarizing plate and the reflected light polarizing plate as a pair after the punching step. Thus, it becomes possible to more reliably prevent a situation where the illumination light polarizing plate and the reflected light polarizing plate each selected from a respective one of two different pairs are attached to the holder, thereby causing deteriorated accuracy in orthogonality between the polarizing directions of the two polarizing plates.

This application is based on Japanese Patent Application Serial No. 2012-262285 filed in Japan Patent Office on Nov. 30, 2012, the contents of which are hereby incorporated by reference.

Although the present invention has been adequately and fully described by way of example with reference to the accompanying drawings, it is to be understood that various changes and/or modifications will be apparent to those skilled in the art. Therefore, unless otherwise such changes or modifications implemented by those skilled in the art depart from the scope of the present invention hereinafter defined, they should be construed as being included therein.

INDUSTRIAL APPLICABILITY

The present invention can provide a reflection property measuring device, and a method of manufacturing polarizing plates for use in the reflection property measuring device.

The invention claimed is:

1. A reflection property measuring device for measuring a reflection property of a sample surface by emitting illumination light onto the sample surface and detecting reflected light as the illumination light after being reflected by the sample surface, comprising:
   an illumination light polarizing plate inserted in an illuminating optical system for guiding the illumination light to the sample surface, and configured to linearly polarize light passed therethrough, in a first polarizing direction;
   a reflected light polarizing plate inserted in a light-receiving optical system for guiding the reflected light to a light detection section, and configured to linearly polarize light passed therethrough, in a second polarizing direction; and
   a holder holding the illumination light polarizing plate and the reflected light polarizing plate in a mutually stacked state in a thickness direction of each of the polarizing plates,
   wherein:
   the holder has one or more fittingly-holding portions for setting respective held postures of the illumination light polarizing plate and the reflected light polarizing plate in the holder;
   the illumination light polarizing plate has one or more fitting portions each fittable to a corresponding one of the fittingly-holding portions of the holder, wherein the illumination light polarizing plate is formed in a shape capable of avoiding an optical path of the reflected light; and
   the reflected light polarizing plate has one or more fitting portions each fittable to a corresponding one of the fittingly-holding portions of the holder, wherein the reflected light polarizing plate is formed in a shape capable of avoiding an optical path of the illumination light, and wherein the fitting portions are provided at positions where they are fitted, respectively, to the corresponding fittingly-holding portions to thereby allow the illumination light polarizing plate and the reflected light polarizing plate to be held by the holder in respective postures where polarizing directions thereof intersect orthogonally, and wherein each of the illumination light polarizing plate and the reflected light polarizing plate has a discriminating portion for discriminating between an obverse side and a reverse side thereof.

2. The reflection property measuring device as defined in claim 1, wherein the holder has a loading surface on which the illumination light polarizing plate and the reflected light polarizing plate are to be placed in a mutually stacked state, and each of the fittingly-holding portions of the holder protrudes in a stacking direction of the illumination light polarizing plate and the reflected light polarizing plate with respect to the loading surface, and each of the fitting portions is a hole or a cutout fittable to the corresponding one of the fittingly-holding portions.

3. The reflection property measuring device as defined in claim 1, wherein the holder has a loading surface on which the illumination light polarizing plate and the reflected light polarizing plate are to be placed in a mutually stacked state, and a protruding portion protruding in a stacking direction of the illumination light polarizing plate and the reflected light polarizing plate with respect to the loading surface, and the discriminating portion is a hole or a cutout provided in each of the illumination light polarizing plate and the reflected light polarizing plate at a position corresponding to the protruding portion, and configured to be fittable to the protruding portion.

4. The reflection property measuring device as defined in claim 1, wherein one of the fitting portions of the illumination light polarizing plate, and one of the fitting portions of the reflected light polarizing plate corresponding to the one fitting portion of the illumination light polarizing plate, are fitted to a common one of the fittingly-holding portions of the holder.

5. The reflection property measuring device as defined in claim 1, wherein the holder holds the illumination light polarizing plate and the reflected light polarizing plate, in such a manner that the illumination light polarizing plate and the reflected light polarizing plate are mutually superposed, while sandwiching the holder therebetween.

6. The reflection property measuring device as defined in claim 1, wherein the reflected light is passed through a central portion of each of the illumination light polarizing plate and the reflected light polarizing plate, whereas the illumination light is passed around the reflected light, or the illumination light is passed through the central portion, whereas the reflected light is passed around the illumination light, and wherein each of the fitting portions of the illumination light polarizing plate and the reflected light polarizing plate is located outside a region through which the illumination light and the reflected light are to be passed.

7. The reflection property measuring device as defined in claim 1, wherein:

the illuminating optical system is configured to guide the illumination light to the sample surface, in such a manner that the illumination light has a ring shape at a position of the illumination light polarizing plate;

the light-receiving optical system is configured to guide the reflected light to the light detection section, in such a manner that a part of the illumination light after being reflected by the sample surface is passed through a central region of the ring-shaped illumination light at the position of the illumination light polarizing plate, to serve as the reflected light;

the illumination light polarizing plate has an opening formed in a central portion thereof to pass the reflected light therethrough; and the reflected light polarizing plate has a plate body superposed on the opening of the illumination light polarizing plate in the direction of the superposition with the illumination light polarizing plate, the fitting portions provided outside a region which surrounds the plate body and through which the ring-shaped illumination light is to be passed, and a connection portion extending from the plate body to the fitting portions.

8. The reflection property measuring device as defined in claim 7, wherein the holder has a light blocking portion formed to extend along the connection portion of the reflected light polarizing plate and disposed in side-by-side relation to the connection portion in the direction of the superposition.

* * * * *